(12) United States Patent
Astani et al.

(10) Patent No.: US 7,779,843 B2
(45) Date of Patent: *Aug. 24, 2010

(54) ADJUSTABLE VAGINAL SPLINT FOR PELVIC FLOOR SUPPORT

(75) Inventors: Aida Astani, Hamburg (DE); Burkhard Peters, Wattenbeck (DE)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/503,961

(22) Filed: Jul. 16, 2009

(65) Prior Publication Data

US 2009/0277456 A1  Nov. 12, 2009

Related U.S. Application Data

(63) Continuation of application No. 11/258,441, filed on Oct. 25, 2005, now Pat. No. 7,628,156.

(51) Int. Cl.
*A61F 6/06* (2006.01)
(52) U.S. Cl. ............... 128/834; 128/836; 128/DIG. 25; 600/29
(58) Field of Classification Search ........... 128/830, 128/834, 836, 885, DIG. 25; 600/29; 602/67, 602/68, 70; 206/501, 509, 515, 516; 220/4.01, 220/4.03, 720, 914
See application file for complete search history.

(56) References Cited

U.S. PATENT DOCUMENTS 2,475,071 A   7/1949  Young
3,247,846 A   4/1966  Fansler
5,297,687 A   3/1994  Freed
6,131,576 A  10/2000  Davis
6,216,353 B1  4/2001  Schenck
6,216,698 B1  4/2001  Regula
6,543,141 B1  4/2003  Biehl
2005/0016545 A1  1/2005  Nissenkorn
2007/0088189 A1  4/2007  Levy

FOREIGN PATENT DOCUMENTS

CA           331100 A      3/1933

(Continued)

OTHER PUBLICATIONS

Kulakov, V.I. et al., Operative Gynecology, A Manual for Physicians, pp. 206-207, The NGMA Publishing House (1998).
Samuelsson, E.C. et al. "Signs of genital prolapsed in a Swedish population of women 20 to 59 years of age and possible related factors", Am. J. Obstet. Gynecol. 180:299-305 (1999).

(Continued)

*Primary Examiner*—Patricia M Bianco
*Assistant Examiner*—Camtu T Nguyen

(57) ABSTRACT

Vaginal splints and methods for their use for treating various pelvic floor conditions are provided. One embodiment of the vaginal splint includes a base portion having a configuration defined by first and second sides, a first connecting portion at a proximal side of the base portion and extending between a first end of each of the first and second sides, and a second connecting portion at a distal side of the base portion and extending between a second end of each of the first and second sides. The splint further includes an adjustable portion coupled to the base portion and positioned substantially adjacent to and distal of the second connecting portion of the base portion. The adjustable portion is removable by a user to thereby change the size of the splint.

6 Claims, 10 Drawing Sheets

FOREIGN PATENT DOCUMENTS

| | | | |
|---|---|---|---|
| CA | 600904 | A | 7/1960 |
| DE | 3720858 | A | 1/1989 |
| DE | 9104155 | U1 | 6/1991 |
| EP | 0084755 | A | 8/1983 |
| RU | 961061 | | 3/1999 |
| RU | 2196519 | C2 | 1/2003 |
| RU | 2232562 | C2 | 7/2004 |
| WO | WO 96/01084 | A1 | 1/1996 |
| WO | WO 2004/045457 | A1 | 6/2004 |

OTHER PUBLICATIONS

Olsen, A.L. et al. "Epidemiology of Surgically Managed Pelvic Organ Prolapse and Urinary Incontinence", Obstet. Gynecol. vol. 89, No. 4, 501-506 (1997).

Winters, J. C. et al. "Abdominal Sacral Colpopexy and Abdominal Enterocele Repair in the Management of Vaginal Vault Prolapse", Urology 55-63 (2000).

Deval, B. et al. "What's new in prolapsed surgery? Current Opinion in Urology" 13:315-323 (2003).

Maher, C.F. et al., "Abdominal sacral colpopexy or vaginal sacrospinous colpopexy for vaginal vault prolapsed: A prospective randomizer study", Am. J. Obstet. Gynecol. 190:20-26 (2004).

Cervigni, M. et al., "The use of synthetics in the treatment of pelvic organ prolapsed. Current Opinion in Urology" 11:429-435 (2001).

Visco, A. C. et al., "Vaginal mesh erosion after abdominal sacral colpopexy", Am. J. Obstet. Gynecol. 184:297-302 (2001).

Boyles, S.H. et al., "Procedures for pelvic organ prolapsed in the united States 1979-1997", American Journal of Obstetric Gynecology 188: 108-115 (2003).

Pang, Man-Wah, et al., "An overview of pelvic floor reconstructive surgery for pelvic organ prolapsed", Journal of Pediatrics, Obstetrics and Gynecology (2003).

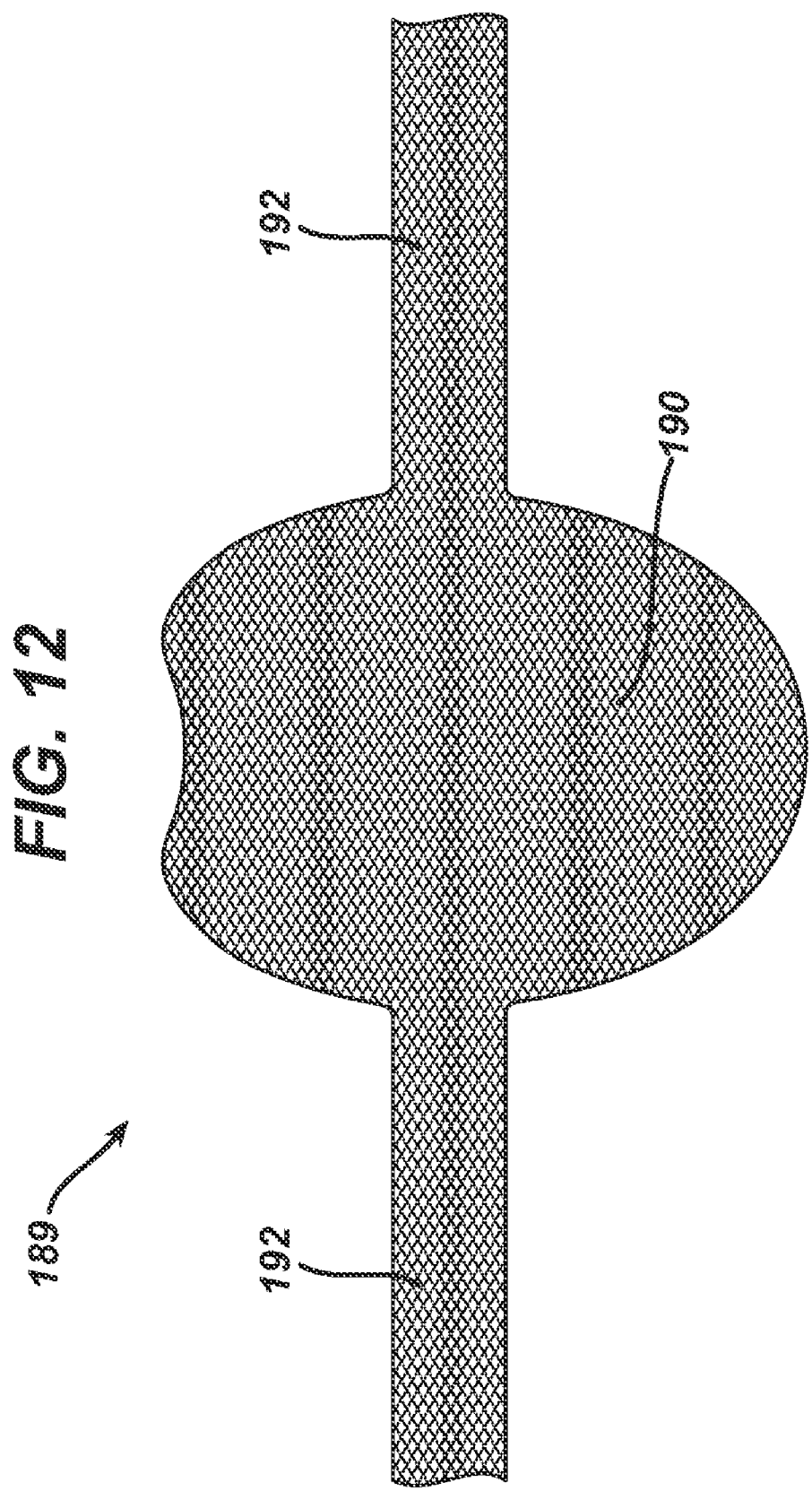

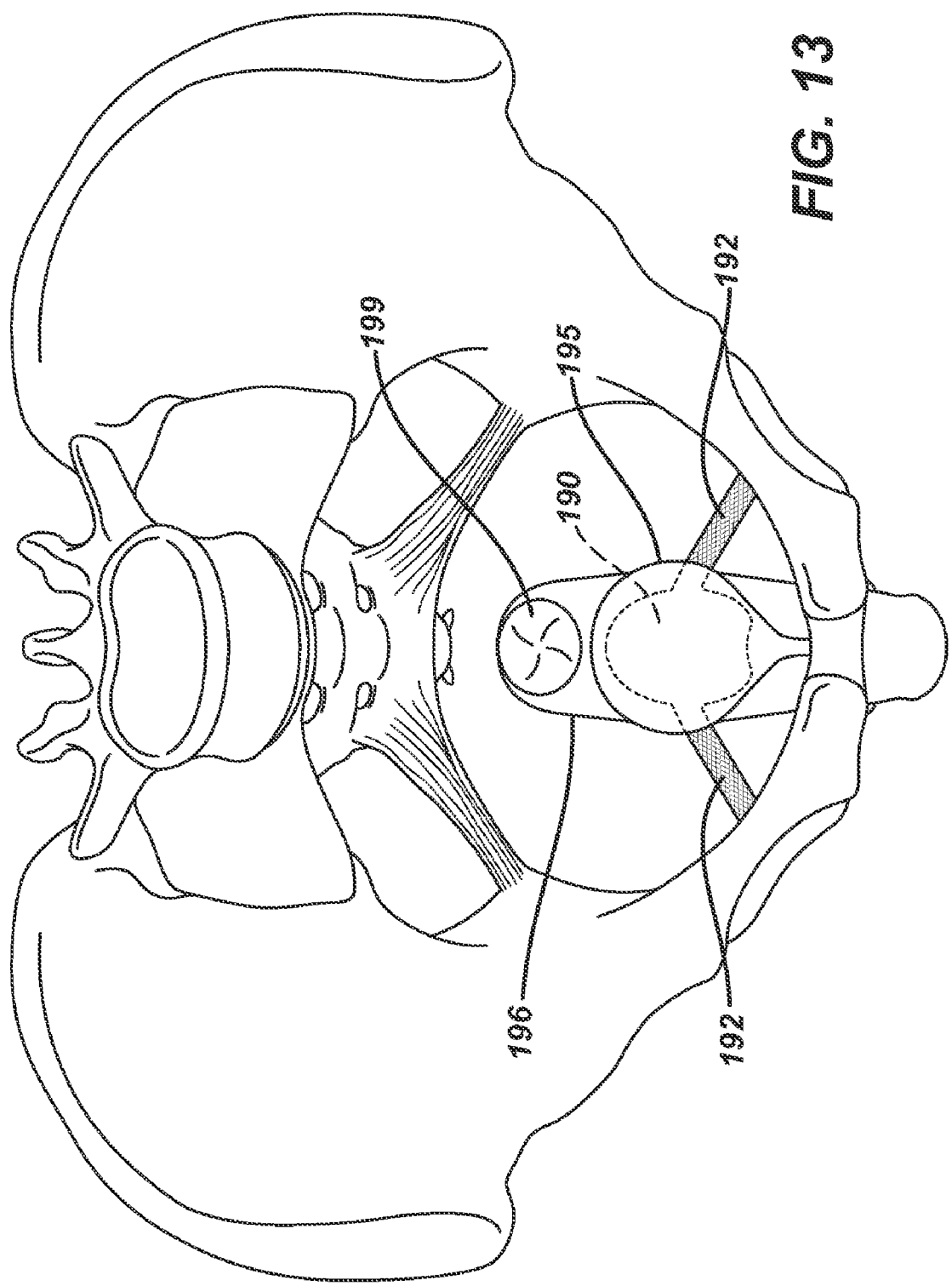

ADJUSTABLE VAGINAL SPLINT FOR PELVIC FLOOR SUPPORT

CROSS-REFERENCE TO RELATED APPLICATIONS

The present application is a continuation of U.S. patent application Ser. No. 11/258,441, filed on Oct. 25, 2005 now U.S. Pat. No. 7,628,156.

BACKGROUND OF THE INVENTION

1. Field of the Invention

The present invention relates to devices suitable for use in repairing various pelvic floor prolapse conditions. More particularly, the present invention relates to adjustable vaginal implants for such use and purposes.

2. Background Discussion

Each year in the USA approximately 200,000 women undergo pelvic organ prolapse surgery. Pelvic organ prolapse generally involves the descent of one or more of the uterus, the bladder or the rectum along the vagina towards (or in extreme cases protruding beyond) the introitus. Women of advancing years, or those that have borne several children are more frequent sufferers of pelvic organ prolapse. Traditional vaginal surgery to address these conditions is associated with a high failure rate of between 30-40%. Complex and elaborate abdominal, vaginal and laparoscopic procedures such as abdominal sacral colpopexy, transvaginal sacrospinous ligament fixation and laparoscopic sacral colpopexy have been developed to reduce the risk of prolapse recurrence. Unfortunately these procedures require a high level of surgical expertise and are only available to a small number of specialist practitioners and therefore to a small number of patients. Details of various procedures currently in use are described in Boyles S H., Weber A M, Meyn L. "Procedures for pelvic organ prolapse in the United States", 1979-1997. American Journal of Obstetric Gynecology 2003, 188; 108-115.

Recently there has been a trend towards the use of reinforcing materials to support a vaginal wall damaged by prolapse. Prosthetic materials such as donor fascia lata, pig dermis and various types of synthetic mesh have been utilized with mixed success. These materials are generally positioned under the vaginal wall or walls and sutured into position.

WO 2004/045457 discloses a different approach that utilizes a prosthetic material in repairing damaged vaginal walls, and subsequently inserts an intra-vaginal splint. The splint is placed into the vagina, and operates to reduce the mobility of the vaginal walls. The repairs are typically made by dissecting either the posterior wall of the vagina or the anterior wall or the vagina or both. A graft of either synthetic material, such as a polypropylene mesh or other fabric, or autologous or analogous material is placed in the dissected area between the vaginal wall and the prolapsing organ. The vaginal incision is then closed by suture or other tissue closure means, at which time the vaginal splint is inserted into the vagina and affixed to either wall. The splint stabilizes the vagina, keeps it elongated, and helps to hold the graft in place by preventing it from sliding or dislodging. Eventually the fascial tissue on each side of the graft will infiltrate into it thereby incorporating it into the body.

An aspect not addressed by WO 2004/045457, however, is the fact that different sized patients will require different sized splints. Simply providing the splints in numerous different sizes is not an economical solution. The present invention addresses this problem and provides improved implants having adjustability features.

SUMMARY OF THE INVENTION

The present invention provides various embodiments of a vaginal splint and methods for treating pelvic floor conditions using such a splint. One embodiment is a vaginal splint sized and shaped for insertion within a vagina of a patient, the splint including a base portion having a configuration defined by first and second sides, a first connecting portion at a proximal side of the base portion and extending between a first end of each of the first and second sides, and a second connecting portion at a distal side of the base portion and extending between a second end of each of the first and second sides. It further includes an adjustable portion coupled to the base portion and positioned substantially adjacent to and distal of the second connecting portion of the base portion, wherein the adjustable portion is removable by a user to thereby change the size of the splint.

The base portion may have an overall substantially trapezoidal configuration, with the first and second connecting portions being substantially parallel to one another, and the second connecting portion having a longer length than the first connecting portion. The adjustable portion may further include at least a first removable apical section having a connecting portion and first and second side portions at first and second ends respectively of the connecting portion. The connecting portion of the first removable apical section is positioned substantially adjacent and parallel to the second connecting portion of the base portion. The first removable apical section may further be removably coupled to the base portion by a joining portion capable of being torn or cut by a user to thereby remove the first removable apical section from the base portion.

In yet another embodiment, the splint further includes a second removable apical portion having a connecting portion and first and second side portions at first and second ends respectively of said connecting portion. The second removable apical portion is removably coupled to a distal side of the first removable apical portion and is positioned substantially adjacent and parallel to the first removable apical portion. The second removable apical portion may further be removably coupled to the first removable apical portion by a second joining portion capable of being torn or cut by a user to thereby remove the second removable apical portion from the first removable apical portion. The splint may have a substantially trapezoidal configuration regardless of which, if any, of the first and second removable apical portions are removed.

In another embodiment, the splint further includes an inflatable member positioned between the first and second sides and first and second connecting portions of the base portion. The inflatable member is inflatable by infusion of fluid therein between a deflated state wherein it does not extend outwardly beyond a top or bottom side of the combination base portion and adjustable portion, and an inflated stated wherein it does extend outwardly beyond the top and/or bottom side of the combination base portion and adjustable portion. The inflatable member may be a balloon made of a material selected from the group consisting of polyurethane, polyester, silicone and rubber.

In yet another embodiment, the distal side of the base portion has one or more recesses therein, and wherein the first removable apical section has one or more protruding elements extending from a proximal side thereof. The one or more protruding elements are removably received within the one or more recesses in the base portion respectively to thereby removably secure the first removable apical portion to the base portion.

This splint may further include a second removable apical portion having a connecting portion and first and second side portions at first and second ends of said connecting portion respectively. The connecting portion of the second removable apical portion is positioned substantially adjacent to, distal of, and parallel to the connecting portion of the first removable apical portion. The second removable apical portion may further have one or more protruding elements extending from a proximal side thereof. The one or more protruding elements are removably received within one or more recesses in a distal side of the first removable apical portion to thereby removably secure the second removable apical portion to the first removable apical portion.

The present invention also provides a method for treating a pelvic floor prolapse condition including providing a splint sized and shaped for insertion within a patient's vagina. The splint includes a base portion having a configuration defined by first and second sides, a first connecting portion at a proximal side of the base portion and extending between a first end of each of the first and second sides, and a second connecting portion at a distal side of the base portion and extending between a second end of each of the first and second sides, and an adjustable portion coupled to the base portion. The adjustable portion is adjustable or removable by a user to thereby change the size of the splint. The method further includes determining a size of a patients vagina, and, based on said determined size, removing or adjusting said adjustable portion if a different size is needed, and inserting the vaginal splint into the patient's vagina.

The adjustable portion may further include at least a first removable apical section having a connecting portion and first and second side portions at first and second ends respectively of the connecting portion, and the removing or adjusting step may further include removing the first removable apical section from the base portion. In yet another embodiment, the adjustable portion is coupled to the base portion by one or more adjustment elements, and the removing or adjusting step further includes moving the adjustable portion relative to the base portion along the adjustment elements closer together or farther apart.

In yet another embodiment, the method further includes, following the inserting step, inflating an inflatable member positioned between the first and second sides and first and second connecting portions of the splint to a state at which the inflatable member extends outwardly beyond a top and/or bottom side of the splint.

The present invention further provides a vaginal splint sized and shaped for insertion within a vagina of a patient, the splint including a base portion having a connecting portion and first and second sides extending in a distal direction from first and second ends of said connecting portion respectively to a free end, an adjustable portion having a connecting portion and first and second sides extending in a proximal direction from first and second ends of said connecting portion respectively to a free end, the adjustable portion being positioned relative to the base portion so that the first and second free ends of the base portion are substantially aligned with and opposed to the first and second free ends of the adjustable portion, and means for adjustably coupling together the base portion and adjustable portion so as to be adjustable relative to one another between first and second positions wherein the distance between the base portion and adjustable portion is different between the first and second portions.

The means for coupling may further include at least first and second adjustment elements each having first and second ends. The first ends are received within recesses in the free ends of the first and second sides respectively of the base portion, and the second ends are received within recesses in the free ends of the first and second sides respectively of the adjustable portion. At least one of the adjustable portion and base portion is slidable relative to the first and second adjustment elements.

In yet another embodiment, the base portion has an overall substantially trapezoidal configuration with the first and second connecting portions being substantially parallel to one another, and the second connecting portion has a longer length than the first connecting portion.

In yet another embodiment, the splint further includes an inflatable member positioned between the first and second sides and first and second connecting portion. The inflatable member is inflatable by infusion of fluid therein between a deflated state wherein the inflatable member does not extend outwardly beyond a top or bottom side of the combination base portion and adjustable portion, and an inflated state wherein it does extend outwardly beyond the top and/or bottom side of the combination base portion and adjustable potion.

BRIEF DESCRIPTION OF THE DRAWINGS

FIG. 12 is an exemplary mesh that can be used in conjunction with a splint for pelvic floor repair;

FIG. 13 illustrates placement of an exemplary mesh within the pelvis for treating a prolapse condition;

DETAILED DESCRIPTION OF THE INVENTION

Before explaining the present invention in detail, it should be noted that the invention is not limited in its application or use to the details of construction and arrangement of parts illustrated in the accompanying drawings and description. The invention as illustrated may be implemented or incorporated in other embodiments, variations and modifications, and may be practiced or carried out in various ways.

Figure 1:
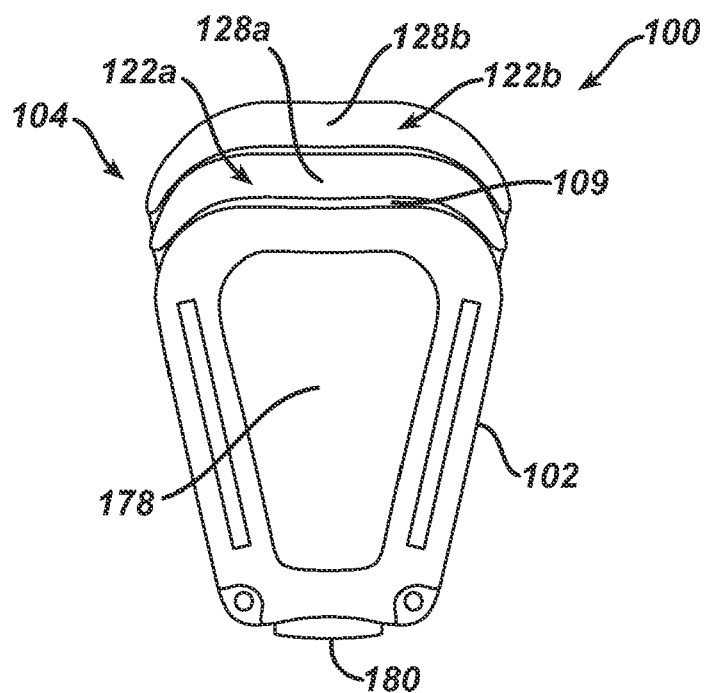
FIG. 1 is a top view illustrating one embodiment of a splint according to the present invention.
Figure 2:
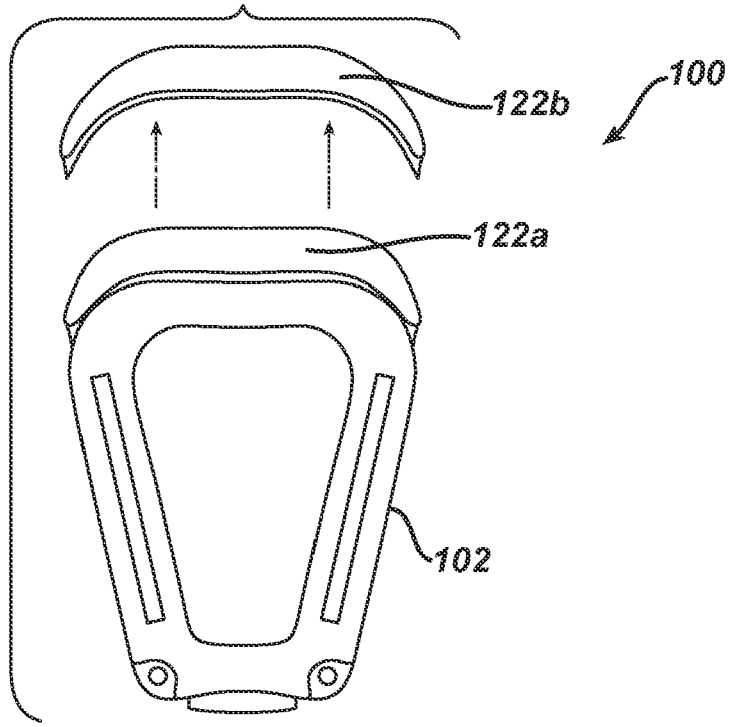
FIG. 2 is a top view of the embodiment of FIG. 1 illustrating removal of one of the apical portions.
Figure 3:
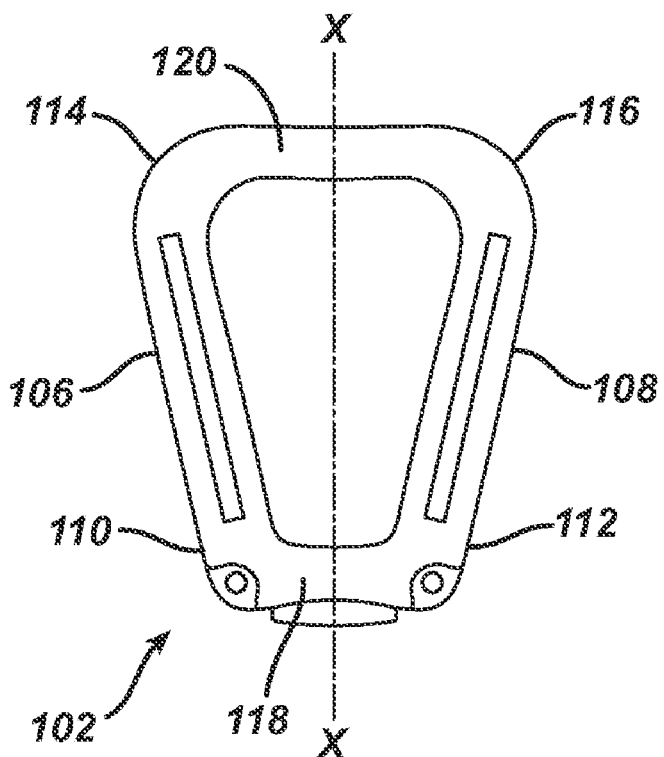
FIG. 3 is a top view of the base portion of the embodiment of FIG. 1.

Referring now to FIGS. 1 to 3, according to one embodiment, the intra-vaginal splint 100 according to the present invention includes a base portion 102 and an adjustable portion 104. The base splint portion includes first and second spaced apart sides 106, 108 each having first 110, 112 and second 114, 116 ends. The sides are connected at their respective first ends by a first connecting portion 118, and at their respective second ends by a second connecting portion 120. The first and second connecting portions or members are preferably of different lengths, but substantially parallel to one another. Further, the second connecting portion is preferably longer than the first connecting portion so that sides 106, 108 are not parallel with each other. In one preferred form, the intra-vaginal base splint is substantially trapezoidal in overall shape. The first connecting portion 118 may include an opening 180 therethrough for accepting an inflatable member, as will be described in more detail below.

The splint may be made out of medical grade silicone, polyurethane, polyvinylchloride (PVC), latex, or Santoprene™, although any other suitable biocompatible materials may be used, such as natural rubbers, and blends or combinations of the previously noted materials. The splint may be formed by liquid injection molding, thermoplastic molding, die cutting, machining, insert molding or any other manufacturing technique well known to those skilled in the art.

Preferably, the splint is resilient and at least partially bendable about its longitudinal axis X-X (see FIG. 3). This feature facilitates easy insertion of the splint into the vagina. The sides 106, 108 may also be reinforced to obtain a more rigid frame with rods, thicker walls, higher durometer plastic, contouring or shaping of the side arms to resist bending, or by selective heat treating of portions and the like.

Figure 4:
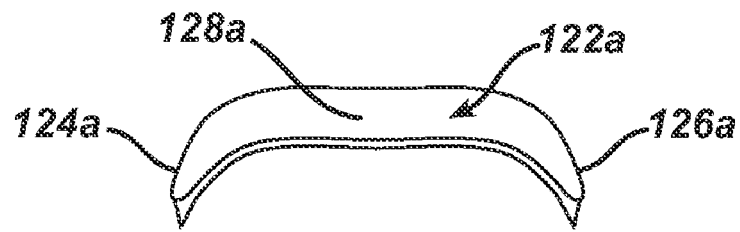
FIG. 4 is a front view of a removable apical portion of the embodiment of FIG. 1.

In the present embodiment, the adjustable portion 104 includes one or more removable apical sections 122a, 122b, a frontal view of which (apical section 122a) is shown in FIG. 4. Each removable section 122a, 122b includes first and second end portions 124a, 126a that extend slightly downwardly from the connecting portion 128a. The connecting portion 128a is substantially straight and parallel with connecting portion 120, and with the central portion 128 of the one or more other removable apical sections. These removable apical sections are connected to one another and to the base splint portion 102 by one or more joining portions or areas 109 of reduced wall thickness to facilitate trimming, tearing, or otherwise separating the apical section from the base portion if necessary for sizing as described further below.

Figure 5:
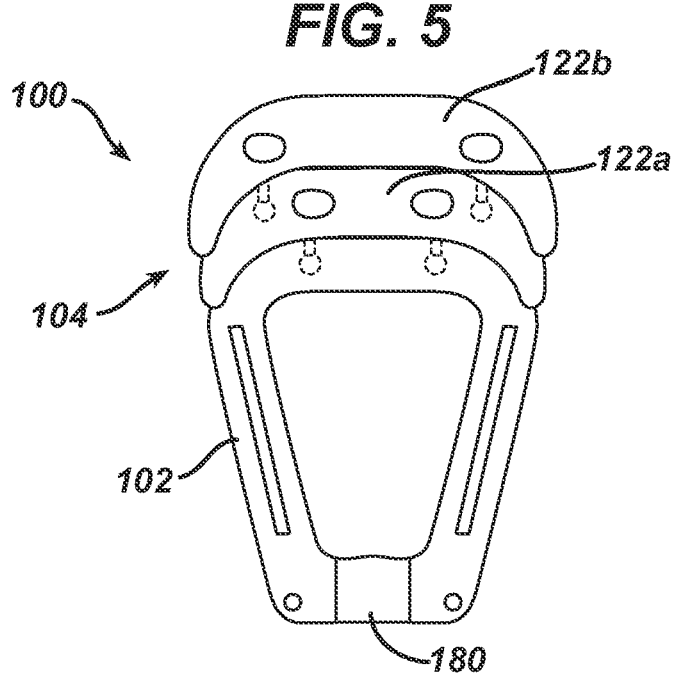
FIG. 5 is a top view illustrating another embodiment of a splint according to the present invention.
Figure 6:
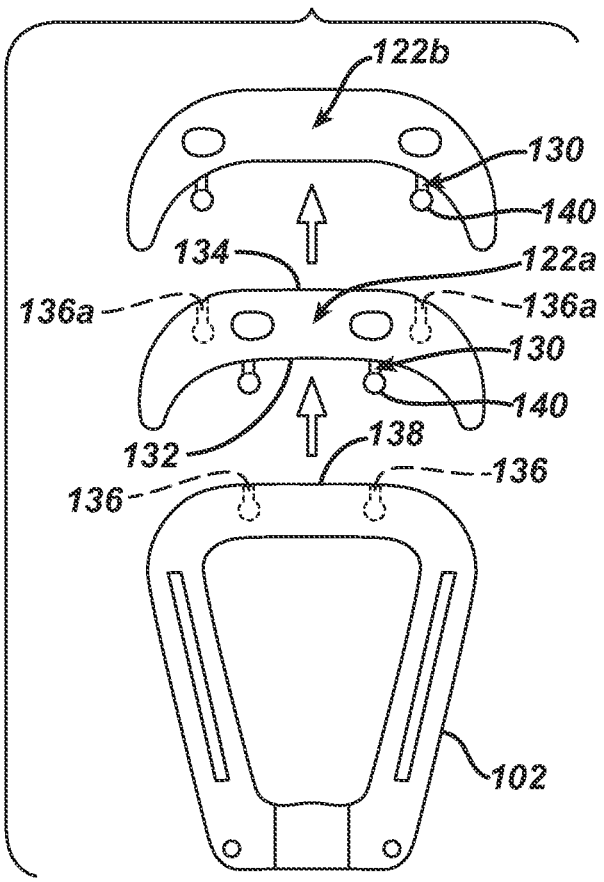
FIG. 6 is a top view of the embodiment of FIG. 5 illustrating removal of the apical portions.

An alternate embodiment of an intra-vaginal splint is shown in FIGS. 4 to 6. The intra-vaginal splint 100 is similar in overall configuration and appearance to the embodiment of FIGS. 1-3, but has a different configuration for the adjustable portion or section 104, and for how the removable apical sections 122a, 122b are coupled with the base portion 102. As shown best in FIG. 6, each removable apical section 122a, 122b includes one or more protruding elements 130 extending outwardly from its proximal side 132. For the most proximal removable section 122a, the one or more protruding elements 130 are designed to mate with corresponding recesses 136 formed in the distal side 138 of the connecting portion 120 of the base portion 102. The protruding elements and corresponding recesses may be of any suitable form and configuration so as to achieve a snug interference fit that will secure the two pieces together. Application of a predetermined force by a user, however, should be able to overcome the interference fit to separate the two pieces. In the illustrated embodiment, the one or more protrusions are substantially rigid, rod-like elements having a bulbous-like portion 140 at their respective ends.

Further, all removable apical sections 122a other than the most distal one 122b have similar recesses 136a formed in the distal side 134 that are positioned and configured so as to accept the one or more protruding elements of the subsequent removable section. As will be described further below, these configurations and means for coupling the removable apical sections to the base portion provide a splint the size of which can be adjusted simply by removing one or more of the removable apical sections.

Figure 7:
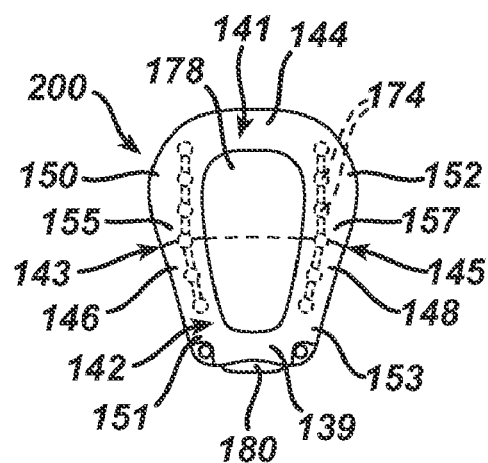
FIG. 7 is a top view of yet another embodiment of a splint according to the present invention.
Figure 8:
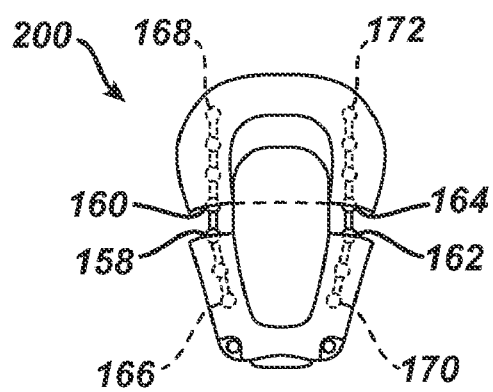
FIGS. 8 and 9 illustrate the embodiment of FIG. 7 as further adjusted to various exemplary positions.
Figure 9:
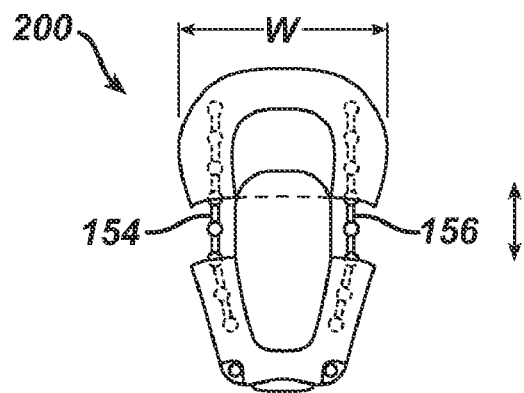
Figure 10:
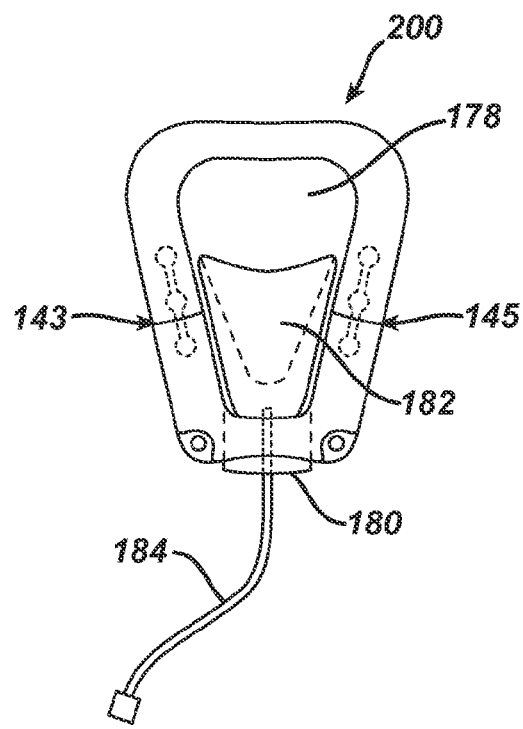
FIGS. 10, 10a and 10b are top, side and front views respectively of a splint having an inflatable member in a deflated state.
Figure 10A:
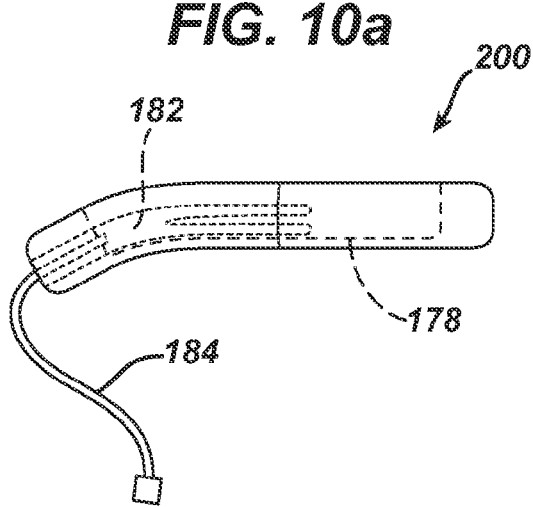
Figure 10B:
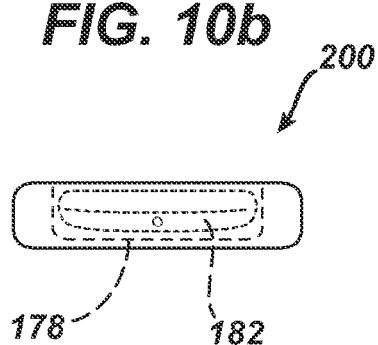

Yet another embodiment of an adjustable vaginal splint 200 is shown in FIGS. 7-9. The splint 200 has a substantially trapezoidal overall configuration defined by a base portion 142 and a single adjustable apical section 144, and more particularly by first and second connecting portions 139, 141 and first and second side members 143, 145. The first and second side members 143, 145 consist of first and second sides 146, 148 that extend in a distal direction from first and second ends 151, 153 of the first connecting portion 139 of the base portion, and first and second sides 150, 152 that extend in a proximal direction from first and second ends 155, 157 of the second connecting portion of the adjustable apical section. These respective sides mate with one another and are adjustably coupled with one another through adjustment elements 154, 156. For each of the first and second adjustment elements 154, 156, first 166, 170 and second 168, 172 ends thereof are received within corresponding cavities or recesses 158, 160; 162, 164 in the base portion and adjustable apical section respectively. The adjustment elements and corresponding recesses form an interference fit as described above in connection with the second described embodiment. In the present embodiment, however, the adjustment elements further include two or more bulbous portions 174 at spaced apart intervals. These bulbous portions provide the tight interference fit, but with application of sufficient force by a user provide for adjustment of the adjustable section relative to the base portion to multiple predetermined distances from one another.

The adjustment mechanism described above may also be used to provide for adjustment of the width W of the apical section 144. In this manner as single apical section can be adjusted to various widths to provide even better adjustability and fit.

Each of the embodiments described above may also include a thin membrane 178 of the like extending across the top and/or bottom sides of the splint so as to substantially cover the area between the first and second connection portions 139, 141 and the first and second side members 143, 145. Each embodiment also preferably further includes an opening, hole or the like 180 that extends through the first connecting portion 118, through which an inflatable member, such as a balloon, can be passed and positioned within the space between the first and second connecting portions and the first and second sides, and the top and bottom membranes if present. The inflatable member may or may not be removably secured to the splint. Further details of such an inflatable member are shown in FIGS. 10-10b and 11-11b.

Attached to the inflatable member 182 is an inflating tube 184 having a lumen that communicates with the interior hollow of the inflatable member and through which fluid can be infused. The inflatable member is preferably positioned within the splint as described above in a deflated state as shown in FIGS. 10-10b. The combination splint assembly is introduced into the vagina and pressurized by fluid infusion (e.g. with saline solution, air or the like) until it reaches a suitable inflated state such as that shown in FIGS. 11-11b. With the addition of the inflatable member, the splint assembly can contact the lateral vaginal walls and superior aspect of the vagina, as well as the upper and lower walls of the vagina. Thus, the splint assembly of the present invention can more completely fill the hollow of the vagina into which it is inserted and contact a greater surface area relative to the prior art. Additionally, since the inflatable member is preferably connected to the splint loosely at only one end, pressure on the inflatable member is not directly translated to pressure on the splint. Consequently, the splint will remain in its desired position and not be subjected to torque forces produced by uneven contact between the balloon and vaginal walls. In this manner, the splint assembly has a hemostatic effect thereby improving wound healing and strength, reduces movement and displacement of the mesh while it incorporates into the vaginal fascial tissues, and avoids the need to use supporting sutures in structures such as the sacrospinous ligament, the uterosacral ligaments or paravaginal tissues. Such sutures are often difficult to place and are associated with significant pain and patient morbidity.

The inflatable member preferably has a minimally extensible wall so that it expands to a large diameter under low pressure so as not to interfere with tissue perfusion. This provides equal pressure between the inflatable member and tissue at all contact points. To the contrary, an inflatable member having a higher inflation pressure and greatly extensible sidewalls is not easily conformable to a body cavity. Additionally, having a relatively thin wall provides good conformability of the inflatable member to the interior slope of the vagina without producing pressure points on the vaginal wall. Thus, the inflatable member conforms to the shape of the vagina instead of the vagina conforming to the shape of the inflatable member. Suitable materials for the inflatable member include polyurethane, polyester, polyethylene, silicones or other similar materials that can be formulated to have similar extension properties. Polyurethane, in particular, can be used to form such an inflatable member having ideal mechanical and geometrical properties, such as good tear, cutting and puncture resistance. The inflatable member may be manufactured by any suitable method, such as blow molding, dip molding, extrusion molding, or injection molding. According to one preferred method, the inflatable member is blow molded on pre-extruded tubing, which is axially and radially stretched in a blow molding process where the polymeric chains are detangled and aligned in parallel.

Figure 14:
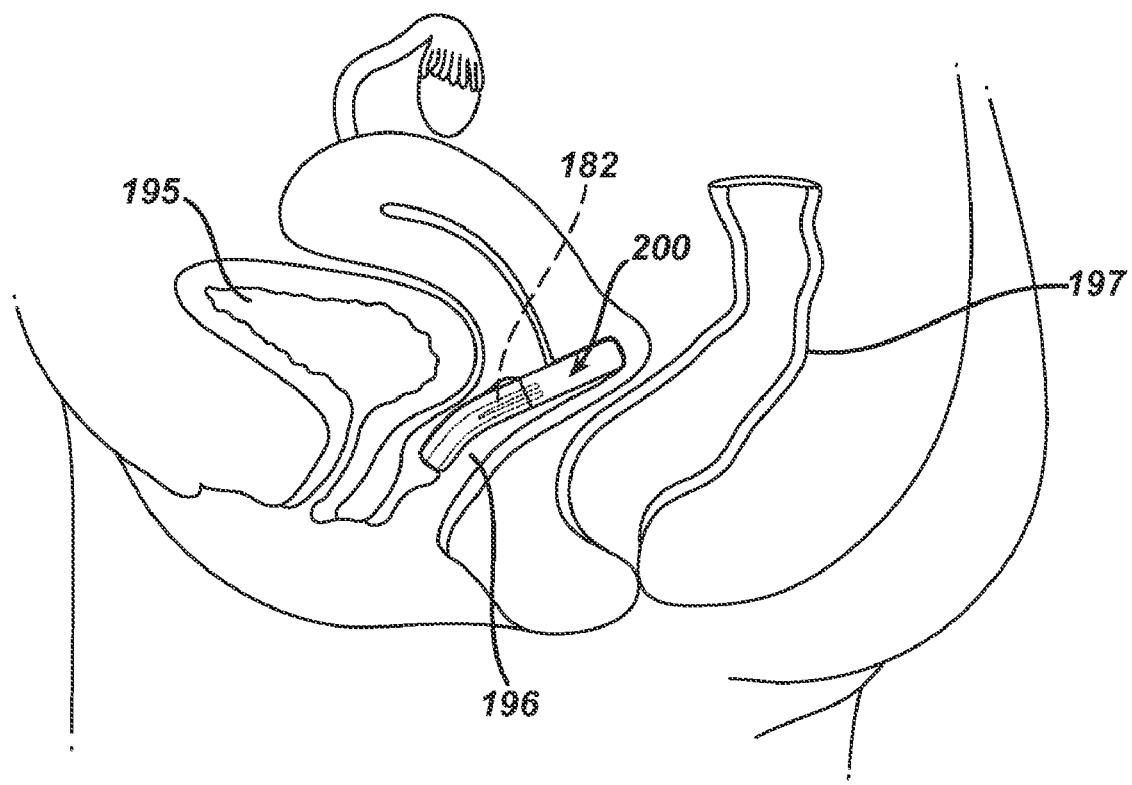
FIG. 14 is a side view illustrating placement of a splint of the present invention within a patient.
Figure 15:
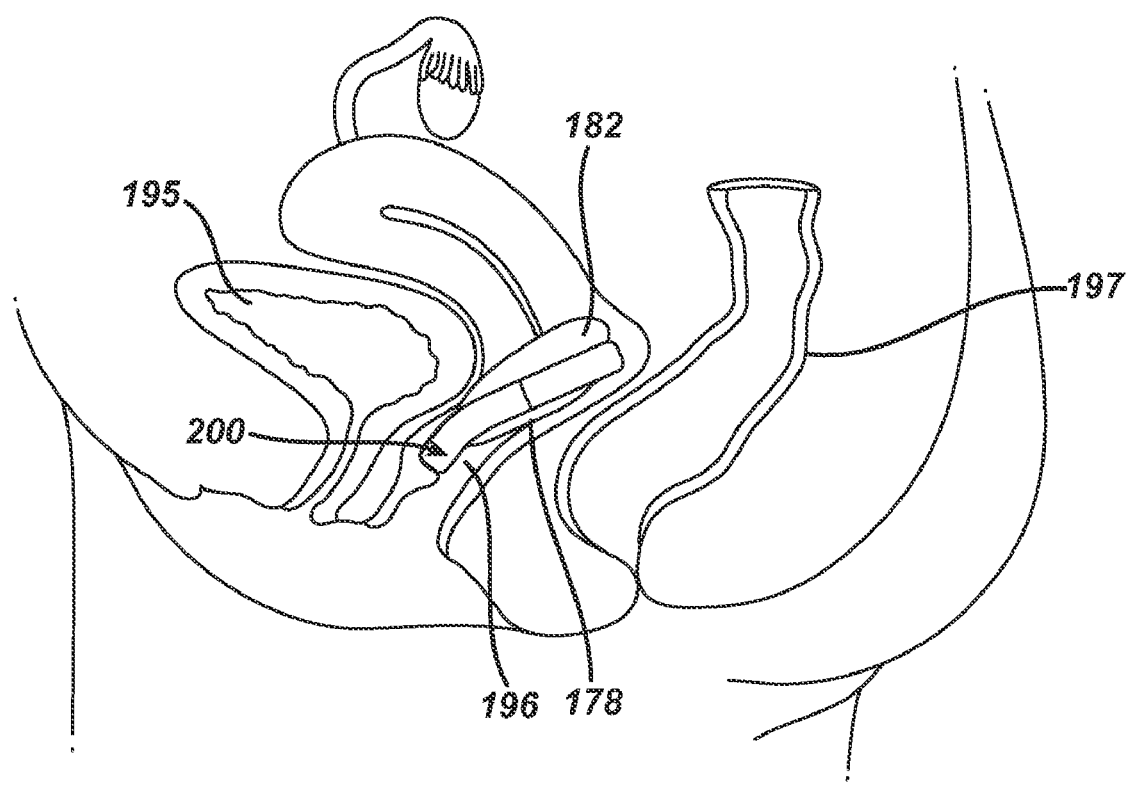
FIG. 15 illustrates the splint of FIG. 13 within a patient, with the inflatable member in an inflated state.

A method for placing the adjustable splint assembly will now be described with reference to FIGS. 13-15. For background reference, each of these figures illustrates various aspects of the pelvic anatomy, including the bladder 195, vagina 196, cervix 199, and rectum 197. An incision is first made in the vaginal epithelium that covers the vaginal wall, and the epithelium peeled and held away from the fascia. Lateral dissection is then carried out to and through the arcus tendinous fascia pelvic on both sides, and into the paravaginal spaces. The fascia is preferably plicated once the epithelium has been mobilized off the fascia wall. A suitable implant, such as a mesh, is then positioned over the defect of the exposed fascia. One exemplary mesh for anterior repair is shown in FIG. 12. This mesh is made of polypropylene, and is manufactured and sold by Ethicon, Inc. of Somerville, N.J. The mesh 189 has a central body portion 190 that is substantially oval in shape, and has lateral extension arms 192. Once properly positioned over the defect, the lateral extension arms 192 of the mesh may be placed into the ipsilateral paravaginal space such that the lateral extension arms come into contact with the inner aspect of the pubic bone. The mesh may then be attached to the fascia by sutures to hold it in place during the remainder of the procedure. Excess vaginal epithelium is then trimmed and the anterior vaginal wall is closed by sutures. The position of the mesh within the pelvis is illustrated in FIG. 13.

Figure 11:
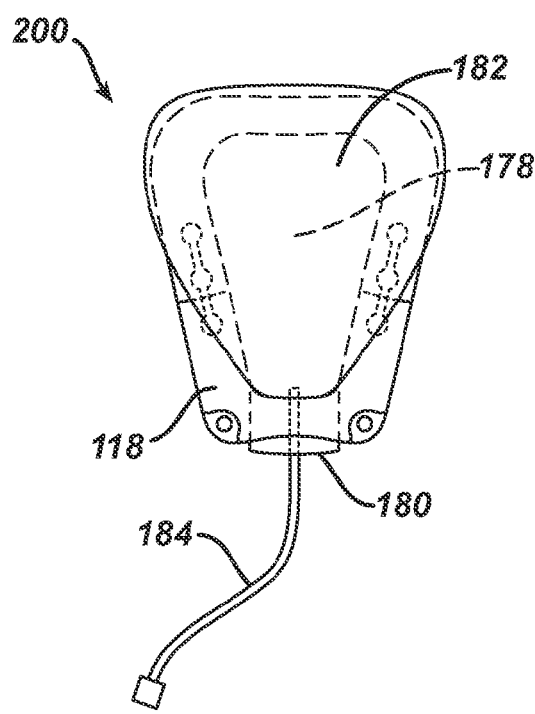
FIGS. 11, 11a and 11b are top, side and front views respectively of the embodiment of FIG. 10 with the inflatable member in an inflated state.
Figure 11A:
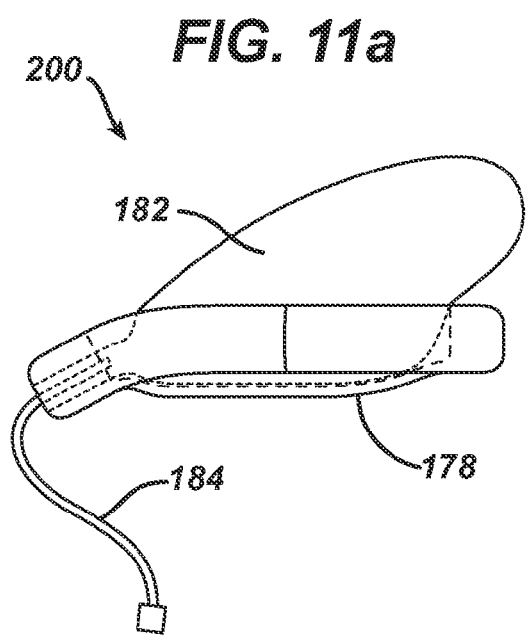
Figure 11B:
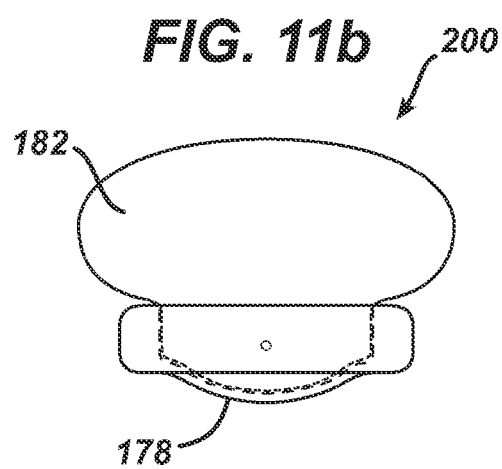

At this point the surgeon determines the size of the vagina. Once the correct size for the intra-vaginal splint has been determined and the adjustable intra-vaginal splint assembly is adjusted to the correct size by trimming or adjusting the adjustable/removable apical section(s) as described above, the splint is inserted into the vagina as shown in FIG. 14. Preferably, the splint may be secured within the vagina by one or more sutures or other attachment means to the epithelium of the vagina either in the anterior, posterior, or lateral walls. The inflatable member is then inflated independently of the splint (as shown in FIG. 15) to prevent the splint from dislodging from its desired position, or otherwise migrating during the healing period. For additional security against accidental movement or dislodgement, one or two suture stitches may be used to attach the splint to the vaginal wall. As shown in FIG. 11, the inflatable member is preferably shaped and sized so that it is larger in diameter at the distal end 210 than at the proximal end 212. This distal end is located in the apex of the vagina near the cervix, which is itself larger in diameter than the introital opening of the vagina and is more easily expandable. The inflatable member is preferably retained in the vagina for a period of 1-2 days, but may remain for a longer period if needed. The inflatable member can then be deflated and removed from the splint and the body. The intra-vaginal splint is preferably retained in the vagina for a period of four weeks, after which time the synthetic mesh has become incorporated into the tissue of each of the respective vaginal walls, and the splint can be removed.

As described above, the inflatable member acts as a tamponade as does the common practice of packing the vagina with gauze. The present device, however, provides several advantages in that it is more readily conformable to the vaginal cavity to provide better coverage for hemostasis, it is smoother and thus less painful, and it is adjustable. Further, as the splint does not absorb blood or other fluids, excessive or unusual bleeding can readily be detected.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A vaginal splint comprising:

a base portion having a configuration defined by first and second sides, a first connecting portion at a proximal side of the base portion and extending between a first end of each of the first and second sides, and a second connecting portion at a distal side of the base portion and extending between a second end of each of the first and second sides, and one or more recesses therein;

an adjustable portion coupled to the base portion and having at least a first removable apical section that further comprises a connecting portion, first and second side portions at first and second ends respectively of the connecting portion, and one or more protruding elements extending from a proximal side thereof, wherein the connecting portion of the first removable apical section is positioned substantially adjacent, distal and parallel to the second connecting portion of the base portion, wherein the vaginal splint is sized and shaped for insertion within a vagina of a patient so as to thereby stabilize the vagina, and wherein the one or more protruding elements are removably received within the one or more recesses in the base portion respectively to thereby removably secure the first removable apical section to the base portion.

2. The splint according to claim 1, further comprising a second removable apical section having a connecting portion and first and second side portions at first and second ends of said connecting portion respectively, wherein the connecting portion of the second removable apical section is positioned substantially adjacent, distal, and parallel to the connecting portion of the first removable apical section.

3. The splint according to claim 2, wherein the second removable apical section has one or more protruding elements extending from a proximal side thereof, and wherein said one or more protruding elements are removably received within one or more recesses in a distal side of the first removable apical section to thereby removably secure the second removable apical section to the first removable apical section.

4. The splint according to claim 2, wherein the splint has a substantially trapezoidal configuration regardless of which, if any, of the first and second removable apical sections are removed.

5. The splint according to claim 1, further comprising an inflatable member positioned between the first and second sides and first and second connecting portions, the inflatable member being inflatable by infusion of fluid therein between a deflated state wherein it does not extend outwardly beyond a top or bottom side of the combination base portion and adjustable portion, and an inflated stated wherein it does extend outwardly beyond the top and/or bottom side of the combination base portion and adjustable portion.

6. The splint according to claim 5, wherein the inflatable member is a balloon comprised of a material selected from the group consisting of polyurethane, polyester, silicone and rubber.

* * * * *